(12) United States Patent
Ueckert

(10) Patent No.: US 11,759,346 B2
(45) Date of Patent: *Sep. 19, 2023

(54) USER-CUSTOMIZABLE ORTHOPEDIC ALIGNMENT DEVICE WITH ALIGNMENT GAP

(71) Applicant: Gregg Edward Ueckert, Austin, TX (US)

(72) Inventor: Gregg Edward Ueckert, Austin, TX (US)

(73) Assignee: Gregg Edward Ueckert, Austin, TX (US)

( * ) Notice: Subject to any disclaimer, the term of this patent is extended or adjusted under 35 U.S.C. 154(b) by 315 days.

This patent is subject to a terminal disclaimer.

(21) Appl. No.: 16/921,707

(22) Filed: Jul. 6, 2020

(65) Prior Publication Data

US 2020/0330257 A1    Oct. 22, 2020

Related U.S. Application Data

(60) Division of application No. 16/856,963, filed on Apr. 23, 2020, now Pat. No. 11,045,344, which is a
(Continued)

(51) Int. Cl.
*A61F 5/058* (2006.01)
(52) U.S. Cl.
CPC ................. *A61F 5/05891* (2013.01)
(58) Field of Classification Search
CPC ...... A61F 5/56; A61F 5/566; A61F 2005/563; A61F 5/08; A61F 5/01; A61C 7/08; A61M 16/04; A61M 16/0415; A61M 16/0418; A61M 16/0434; A61M 16/0436; A61M 16/0443; A61M 16/0445; A61M 16/0447;
(Continued)

(56) References Cited

U.S. PATENT DOCUMENTS

| 8,567,408 B2 | 10/2013 | Roettger |
| 8,667,971 B2 | 3/2014 | Makkar et al. |

(Continued)

OTHER PUBLICATIONS

International Search Report and Written Opinion for PCT Application No. PCT/US2021/028624, dated Aug. 12, 2021, 9 pages.
(Continued)

*Primary Examiner* — Ophelia A Hawthorne
(74) *Attorney, Agent, or Firm* — SPRINKLE IP LAW GROUP

(57) ABSTRACT

A user-customizable orthopedic alignment device (OAD) that includes a formable mouthpiece which has an alignment gap that is aligned with the user's canine teeth when the device is placed in the user's mouth. The OAD has moldable material that cover the user's molars and may cover the front teeth. The alignment gap is provided to allow an alignment member to be positioned laterally between the user's canine teeth during molding of the moldable material. The moldable material may be positioned on a frame that includes living hinges that allow the frame and mouthpiece to flex and adjust to the specific spacing between a user's right and left molars. After the moldable material has been molded to the user's teeth, inserts can be positioned in the alignment gap in some embodiments to provide cushioning between the canine teeth when the OAD is used.

6 Claims, 12 Drawing Sheets

Related U.S. Application Data continuation-in-part of application No. 16/362,301, filed on Mar. 22, 2019, now Pat. No. 10,675,127.

(58) Field of Classification Search
CPC .......... A61M 16/0456; A61M 16/0479; A61M 16/0493; A61M 2205/583; A61M 25/04
See application file for complete search history.

(56) References Cited

U.S. PATENT DOCUMENTS

| | | |
|---|---|---|
| 8,667,972 B2 | 3/2014 | Makkar et al. |
| 10,675,127 B1 * | 6/2020 | Ueckert .................. A61C 19/04 |
| 11,045,344 B2 | 6/2021 | Ueckert |
| 2010/0206314 A1 | 8/2010 | Brown |
| 2011/0209714 A1 | 9/2011 | Makkar et al. |
| 2014/0093834 A1 | 4/2014 | Andary |
| 2014/0238418 A1 | 8/2014 | Turkbas |
| 2015/0173935 A1 | 6/2015 | Cooper |
| 2019/0076227 A1 | 3/2019 | Charkhandeh |
| 2020/0297521 A1 | 9/2020 | Ueckert |

OTHER PUBLICATIONS

International Preliminary Report on Patentability for PCT Application No. PCT/US2020/024229, dated Oct. 7, 2021, 7 pages.
International Search Report and Written Opinion for PCT Application No. PCT/US2020/024229, dated May 7, 2020, 8 pgs.
Office Action for U.S. Appl. No. 16/856,963, dated Dec. 15, 2020, 15 pgs.

* cited by examiner

USER-CUSTOMIZABLE ORTHOPEDIC ALIGNMENT DEVICE WITH ALIGNMENT GAP

RELATED APPLICATIONS

This application is a divisional application and claims priority to U.S. patent application Ser. No. 16/856,963, entitled "User-Customizable Orthopedic Alignment Device with Alignment Gap", filed Apr. 23, 2020 (now issued as U.S. Pat. No. 11,045,344), which is a continuation in part and claims priority to U.S. patent application Ser. No. 16/362,301, entitled "User-Customizable Orthopedic Alignment Device with Alignment Gap", filed Mar. 22, 2019 (now issued as U.S. Pat. No. 10,675,127), all of which are fully incorporated herein by reference for all purposes.

BACKGROUND

Field of the Invention

The invention relates to manufacturing and using orthopedic alignment devices that are designed to maintain an optimized orthopedic alignment of the upper and lower jaws and thereby promote optimized orthopedic alignment of the head and upper cervical spine.

Related Art

Protective mouthpieces have long been used by athletes for the purpose of avoiding damage to their teeth. These mouthpieces may also be intended to reduce the effects of concussive impacts to the head and the jaw. More recently, it has been discovered that mouthpieces may, by maintaining a desired position of the lower jaw with respect to the upper jaw, affect an athlete's performance and well-being. Conversely, poor head position induces torque in the upper cervical spine, creating shear on the central nervous system (CNS) and limiting range of motion in the major joints of the body. This prevents optimal physiologic output and presents an increasing risk of injury through accommodation to the restricted movements and less than optimal physiologic alignment.

There are techniques that are practiced by trained medical professionals to determine an optimized, orthopedically aligned position of a person's jaw, and to form a custom-fit orthotic device that can be used to maintain the optimized, orthopedically aligned position of the jaw. Because these techniques require the skills of a trained medical professional, however, they are not widely available, and the associated costs may make widespread distribution cost-prohibitive. It would therefore be desirable to provide systems and methods for orthopedically aligning a user's jaw with a mouthpiece-type product that can be molded to fit the user's jaw by the user himself rather than requiring a trained technician to custom-fit the device.

SUMMARY OF THE INVENTION

This disclosure is directed to systems and methods relating to the improvement of a person's orthopedic alignment, from the head, descending down the postural chain to the feet by means of a user-fit mouthpiece. (The user may alternatively be referred to herein as a wearer.) This device can improve physiologic performance and reduce injuries that are directly related to poor head position which causes poor alignment of the postural chain. The improvement is achieved through the improvement of the Cranio-Cervical/Cranio-Mandibular (CC/CM) relationship as compared to situations in which conventional mouthpieces are used.

One exemplary embodiment comprises a mouthpiece-type orthopedic alignment device (OAD) that is designed to enable a user to fit the device to his or her own jaws and teeth. The OAD is used in conjunction with means to properly position the lower jaw with respect to the upper jaw when the OAD is fitted (molded to the upper and lower teeth). The "proper" positioning of the upper and lower jaws, as referred to here, is positioning that will induce the user's upper cervical spine to move toward an aligned position, which will in turn induce alignment of the remainder of the user's postural chain.

One embodiment comprises a user-customizable OAD that includes a formable mouthpiece which is adapted to be positioned in the user's mouth between the upper and lower teeth. The OAD includes a moldable mouthpiece having at least a right section and a left section to be molded to the user's molars, and may also have a front section to be molded to the front teeth. Each of these sections has a bite portion which contacts bite surfaces of the user's teeth. The moldable mouthpiece forms an alignment gap that is positioned generally in alignment with the user's canine teeth when the device is placed in the user's mouth (with the left and right bite portions positioned between the user's upper and lower molars). The alignment gap enables unobstructed positioning of an alignment member laterally between the user's canine teeth. The right and left sections of the overmold comprise a formable material which is adapted to be temporarily softened, molded to the user's teeth, and hardened in a shape that conforms to the user's teeth. The formable material may be, for example, a thermoplastic material which is adapted to be softened by heating and hardened by cooling. When the moldable mouthpiece is temporarily softened, the mouthpiece is positioned in the user's mouth with an alignment member. The alignment member is positioned in the alignment gap and between the user's upper and lower teeth. Contact pressure between the user's teeth and the alignment member urges the jaw toward an orthopedically aligned position. The overmold hardens and is molded to the user's teeth in this position.

When the formable mouthpiece is positioned in the user's mouth, the right section and the left section are positioned against respective ones of the user's upper and lower molars. The formable mouthpiece may also have a front portion which is positioned against the user's upper and lower front teeth. The alignment gap of the formable mouthpiece is between the front section and the right and left sections of the formable mouthpiece. In one embodiment, the user-customizable OAD also includes a frame on which the moldable material is mounted (e.g., embedded in or otherwise affixed to the frame). The frame includes may include living hinges that enable the frame to flex at corresponding points so that the spacing between the right and left sections of the moldable mouthpiece can be adapted to the wearer's teeth. The user-customizable OAD may have one or more alignment gap inserts that are configured to fit within the alignment gap in the overmold. The alignment gap inserts may be made of a thermoplastic material which is adapted to be softened by heating and hardened by cooling.

Numerous other embodiments are also possible.

BRIEF DESCRIPTION OF THE DRAWINGS

Other objects and advantages of the invention may become apparent upon reading the following detailed description and upon reference to the accompanying drawings.

Figure 1A:
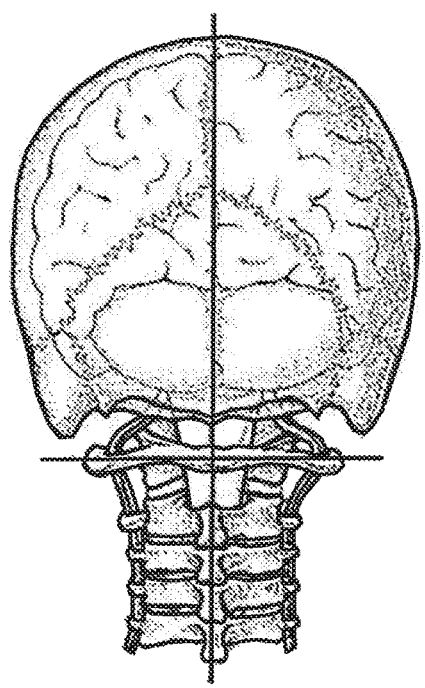
FIGS. 1A and 1B are diagrams illustrating exemplary posterior views of the cervical spine in an aligned position and a non-aligned position, respectively.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims. Further, the drawings may not be to scale, and may exaggerate one or more components in order to facilitate an understanding of the various features described herein.

DETAILED DESCRIPTION OF EXEMPLARY EMBODIMENTS

One or more embodiments of the invention are described below. It should be noted that these and any other embodiments described below are exemplary and are intended to be illustrative of the invention rather than limiting.

As described herein, various embodiments of the invention comprise systems and methods for promoting optimized orthopedic alignment of the head and upper cervical spine through the use of user-fitted OAD's that maintain improved CC alignment via an improved CM orthopedic alignment of the TMJs and upper and lower jaws As noted above, the position of a person's jaw may affect his or her well-being and performance. Various studies have been conducted in relation to the effect of jaw position on performance. For example, U.S. Pat. No. 8,667,972 to Makkar, et al. (which is incorporated herein by reference) briefly notes several articles on the use of mouthpieces to maintain a physiological resting position of the jaw and thereby enhance physical performance. The U.S. patent application filed Feb. 27, 2017 by Ueckert (which is incorporated herein by reference) also discusses this subject, as well as alignment of the skull with the spine (CC alignment) to ensure that neural shear (which is used herein to refer to the stress on the spinal cord at the skull and upper cervical vertebrae) has been minimized or relieved. The CC alignment and minimized neural shear affect the positioning of the mandible with respect to the skull (CM positioning).

Using the methodologies discussed by Makkar and Ueckert, a person's performance can be maximized, and their risk of injury can be minimized. Both Makkar and Ueckert involve the use of transcutaneous electric neural stimulation (TENS) by a trained medical professional such as a dentist or orthodontist to determine an orthopedically optimized CM position. When the jaw is in the orthopedically optimized position, a bite registration is taken. Impressions of the person's teeth are taken and are used to form positive molds of the patient's upper and lower teeth. These positive molds are mounted on an articulator, and the bite registration is used to align the positive molds to the orthopedically optimized bite position. Finally, a mouthpiece or OAD is formed between the upper and lower molds. Use of this OAD holds the jaw in the orthopedically optimized CM position, so that the optimum CM alignment is induced.

While these techniques achieve optimized performance for the patient, the complex, detailed procedures and the involvement of medical professionals may increase the cost of the techniques to the point that they are not practical solutions for many people. For instance, many schoolchildren who participate in sports use protective mouthpieces, but are not able to afford the cost of having a mouthpiece custom made. It is common in this type of situation for people to purchase an over-the-counter mouthpiece that can be molded to the user's teeth. Typically, the mouthpiece is softened in hot water, placed in the user's mouth, pressed against the user's teeth, and allowed to cool and harden enough to retain its shape while still remaining flexible. When molding these conventional over-the-counter mouthpieces, there is no way to ensure that the lower jaw is in a beneficial position, so the mouthpiece commonly holds the jaw in an up-and-back position in which the TMJs are not fully decompressed. Additionally, this position does not provide any performance benefits to the user and can actually negatively affect the user's performance.

It should be noted that "harden", as used herein, is used to refer to the stiffening of the material, and does not indicate that the material becomes completely rigid or inflexible. Put another way, "hardening" refers to the changing of the material from a first, moldable state in which the shape of the material be conformed to the teeth to a second, firm state in which the shape of the material does not change, except that it may flex somewhat from its molded shape. "Softening", as used herein, refers to the preparation of the material to be molded, such as by heating the material, or mixing components of the material, which will then remain moldable for period of time before curing and stiffening in a molded shape.

Embodiments of the present invention overcome this problem by using one or more alignment members that maintain a beneficial alignment of the lower jaw with respect to the upper jaw during the molding of the mouthpiece-type OAD to the teeth. In one embodiment, the alignment members consist of a substantially rigid bar that is positioned laterally (i.e., extending left-to-right, generally perpendicular to the anterior-posterior direction), typically adjacent to the user's canine teeth so that the user's lower teeth and jaw are maintained in an orthopedically aligned position. A moldable portion of the OAD has an alignment gap that is oriented to allow the alignment members to be positioned without obstruction between the upper and lower teeth when the moldable portion is positioned in the user's mouth. The moldable portion is softened and placed in the user's mouth, and the alignment member is positioned laterally within the gap between the user's teeth. The user lightly bites down with the alignment member contacting the upper and lower teeth.

The alignment member is positioned laterally (left-to-right), generally between the user's canine teeth, so that the upper and lower teeth are comfortably spread. In one embodiment, the alignment member is distal to upper teeth 6 and 11, and lower teeth 22 and 27, although it may be positioned to contact other teeth for some users. (It should also be noted that these numbers correspond to adult dentition, and other identifiers, e.g., teeth c, h, m and q, are applicable to pediatric dentition). The contact of the bar with these teeth causes the lower jaw to move so that the teeth are aligned in a desired position (e.g., with the corresponding gaps between the upper and lower teeth to be aligned vertically, and with teeth 6, 11, 22 and 27 substantially aligned vertically) as the moldable portion of the OAD hardens. This positioning is typically an improvement over the normal resting jaw position when molding a conventional mouthpiece (i.e., a position in which the lower front teeth are posterior to the upper front teeth). When the moldable portion has hardened, the alignment member can be removed from the teeth. In this embodiment, inserts are then positioned in the alignment gap and are locked into position by retaining features in the inserts and the molded portion of the OAD. After the inserts are positioned in the alignment gap, the inserts can be softened to mold them to the canine teeth.

Before describing exemplary embodiments of the invention, it may be helpful to explain some aspects of the relationship between CC alignment, CM alignment and their impact on performance and minimizing risk of injury. The spinal cord emerges from the skull through the foramen magnum—the large opening at the base of the skull—and extends through the vertebrae, including the uppermost cervical vertebra (referred to as C1, or the "atlas") and the second cervical vertebra (referred to as C2, or the "axis"). The atlas and axis enable 70% of the movement of the skull with respect to the spine.

Figure 2:
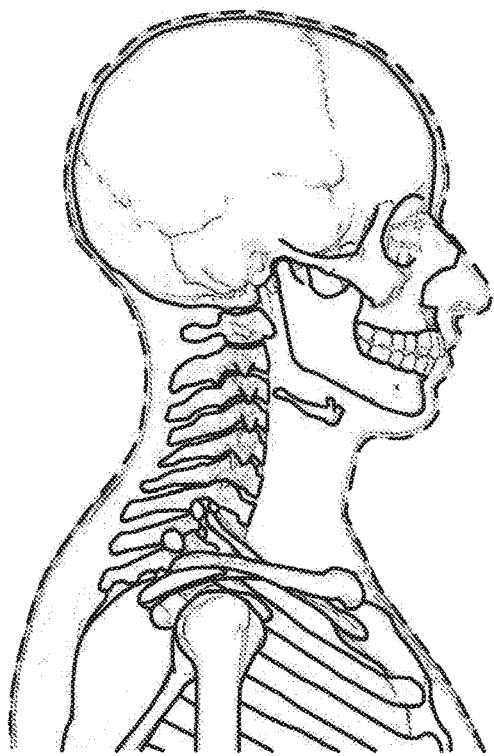
FIG. 2 is a diagram illustrating an exemplary lateral view of the cervical spine in an aligned position.

When the skull and cervical vertebrae are perfectly aligned (see FIGS. 1A and 2), neural shear on the spinal cord within the atlas and axis is minimized. Whenever the skull moves away from this concentrically aligned position, the spinal cord is moved with it, which places torque on the central nervous system. This torque is induced by a direct physical connection of the atlas and axis via a connective tissue bridge to the dura mater, which is a thick membrane that is the outermost of the three layers of the meninges that surround the brain and the spinal cord. The dura mater functions as a sort of "skin" that covers and protects the brain and central nervous system. When the dura mater is stretched or twisted by movement of the head or neck away from optimal alignment, torque is induced into the central nervous system. If the shear stress on the spinal cord is too high, range of motion is immediately limited to prevent further shear of the central nervous system and nerve tissue. Pain emanating from nociceptors can also signal the brain to limit the body's range of motion. This pain sensation inhibits further movement and corresponding stress on the spinal cord.

Figure 1B:
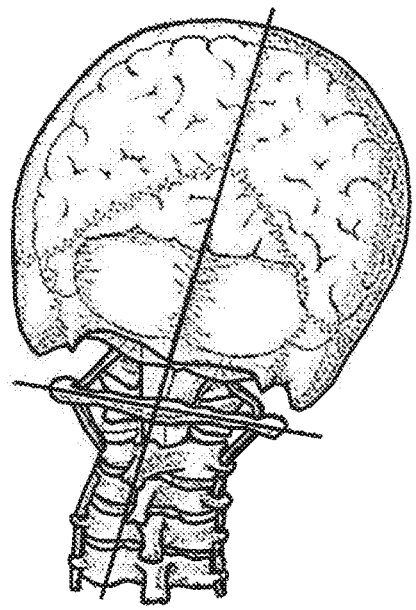
Figure 3:
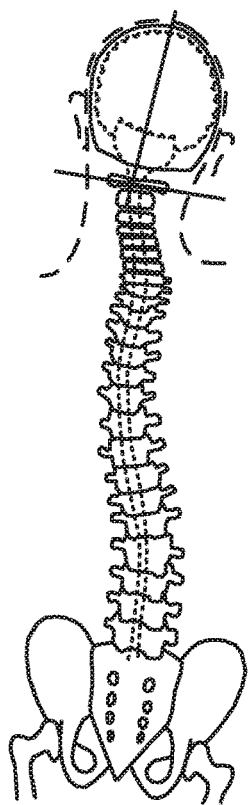
FIG. 3 is a diagram illustrating an exemplary posterior view of the full spine in a non-aligned position.

For example, if person's head is side bent and turned to the left, shear forces will be placed on the brachial plexus of nerves that innervate the right arm. The range of motion of the right shoulder will be limited to prevent further shear from occurring, and the induced compression and misalignment of the nerves can cause paraesthesia in the affected arm into the hand. This misalignment can descend down the postural chain, affecting alignment down to the feet (see FIG. 3). In addition to creating shear forces or compression on the person's nerves and consequent pain, the misalignment can cause constriction of the vertebral artery (see FIG. 1B), potentially resulting in problems such as vascular migraine headaches and high blood pressure, as the heart pumps harder to adequately perfuse blood into the brain.

The jaw joint is the most unique and most used joint in the body. This joint functions as a rotational joint in the first 20 mm of opening, and in the last 20-25 mm of opening translation of the joint occurs. During this translation, the condyle of the mandible moves out of the glenoid fossa to reach maximum opening. The lower jaw can move in six translational directions—up/down, forward/backward, and side-to-side. In addition to this, it can also move in the same rotational directions as an airplane, referred to as pitch, yaw and roll. For example, if person closes his jaw and the front teeth touch before the back teeth, the lower jaw will pitch up in back until the back teeth touch. If the front left teeth touch on one side first before the other side, the jaw will yaw away from the premature contact to avoid the interference. And if the back teeth on the right side touch before the back teeth on the left side touch the jaw will roll up on the left side until the posterior teeth touch. When the lower jaw has to pitch yaw or roll, it creates compression in the TMJs, which results in torque in the upper cervical spine (C1 and C2), immediately developing neural shear. To manage this shear, the jaw has to be balanced in all 6 directions. This is accomplished using the OAD.

The concept of interaction or interdependence of the CM alignment and the CC alignment is sometimes referred as the 50-50 principle, pioneered by Dr. Mariano Rocabodo. The commonality between the relationships is the skull, and changing one of the alignments affects the other—the Action/Reaction Law. If the alignment of the lower jaw and upper jaw is improved, the alignment of the cervical spine also improves. Conversely, if the alignment of the cervical spine is improved, the alignment of the upper and lower jaws will improve.

Figure 4:
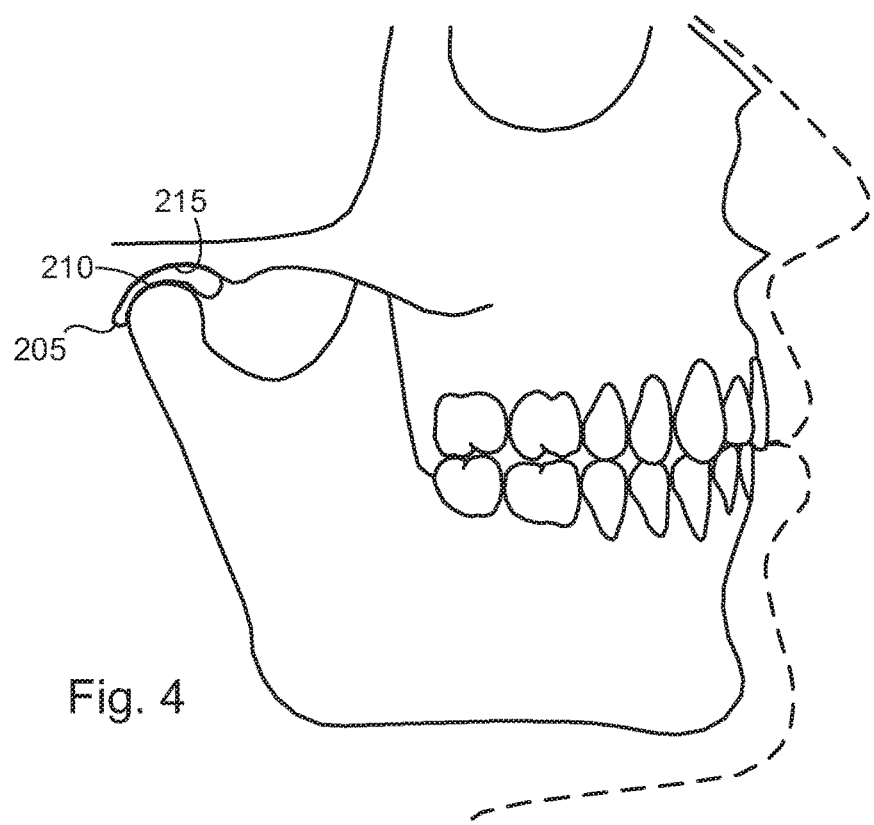
FIG. 4 is a diagram illustrating a patient's jaw in a position that is not orthopedically optimized, and has ADD in the TMJ.

In a habitually (but not optimally) aligned CC/CM relationship, when a person's jaw closes, the upper front teeth are positioned in front of (anterior to) the lower front teeth (see FIG. 4). Conventional user-fitted mouthpieces hold the jaw in a position which is close to this habitual alignment, although the teeth are spaced slightly farther apart. The posterior teeth on the right and left contact at the same time without generating any pitch/yaw/roll before the anterior teeth touch. The right and left TMJ articular discs are stable and reduced without any anterior displacement in the glenoid fossa, and C1 and C2 are concentrically aligned without any subluxation or rotation.

In a habitual, subluxated alignment as shown in FIG. 4, the lower jaw must move up and back to seat the posterior teeth. This compresses the TMJs, leading to ADD and causing subluxation of C1/C2, forward head posturing with possible rotation and side bending, and cascading misalignment down the postural chain. This up-and-backward movement of the jaw also causes occlusion of the person's airway by limiting tongue space. Additionally, the person's tongue moves backward to avoid being bitten, which further occludes the airway, leading to obstruction while sleeping and increasing the incidence of snoring or obstructive sleep apnea. In response to the occlusion of the airway and the collapse of the jaw relationship due to loss of posterior bite support, descending subluxation of the postural chain occurs as the person's head moves forward. This is dictated by the action/reaction law, creating obstructions in joint movement (like Femoral-Acetabular-Impingement or FAI) and helping maintain a more open airway. This forward movement of the head in turn affects the central nervous system by placing torque on the brain stem, generating neural shear in the upper cervical spine, and causing the atlas and axis to subluxate, which also limits the range of motion in the major joints.

Proprioception is the sense of the relative position of neighboring parts and strength of effort being employed in movement of the body parts. This term is therefore used to describe the sensory information that contributes to the sense of position and movement of the jaw. The receptors from our muscles and joints innately inform us and give us body awareness and provide information on how we are moving.

The proprioceptive system is located primarily in the cerebellum (the balance center of the brain) and it works closely with the vestibular system and tactile system. The spinocerebellum regulates tone, posture and equilibrium by receiving sensory impulses from proprioceptors, tactile receptors, visual receptors and auditory receptors. In the case of the jaw, it is the trigeminocerebellar tract that provides the proprioceptive efferent connection to the spinocerebellum. This tract conveys proprioceptive information from the jaw muscles and the TMJs to the spinocerebellum. It also carries the sensory impulses from the periodontal tissue (the ligaments and tissue that supports the teeth in the jaw bone) to the spinocerebellum.

The proprioception of the relationship of the jaw, TMJs and teeth is provided directly to the cerebellum. When the posterior teeth (molars and premolars) make contact, proprioception via the trigeminocerebellar tract communicates with the spinocerebellum instantly, using the information to effect head position. This occurs, on average, about 3000 times each day. Consequently, if a person's jaw is out of alignment, the position of the person's head will also be out of alignment. If, on the other hand, the person's jaw is more optimally aligned, the person's CC/CM alignment is corrected so that his or her head position is not subluxated, but is instead more orthopedically aligned. More specifically, it can be held in an orthopedically aligned position in which neural shear is reduced and the head is back at a balanced point, initiating a descending cascade of realignment down the postural chain. This results in improved range of motion of major joints, improved balance, more patent airway, better motor recruitment and reduced risk of injury. The improvement is immediate and can be assessed using normal range-of-motion tests for the upper cervical spine, lower cervical spine, shoulders and hips. In the case of patients who have pain that derives from subluxation of the CC/CM complex, improved alignment of this complex reduces neural shear and immediately decreases pain in joints that were limited in range of motion.

In the methods of Makkar and Ueckert, TENS is applied to the patient's jaw muscles to relax the muscles and to "deprogram" them. This is done because the patient has created an engram pattern of muscle contraction to lift the lower jaw and couple the posterior teeth into a position posterior to the physiological resting position (see FIG. 4). When the muscles have been deprogrammed, the jaw will close to a more optimized position that is related to the CC alignment of the upper cervical vertebrae. In this position, the front teeth will be more aligned with each other vertically (see FIG. 5), rather than having the upper front teeth anterior to the lower front teeth (see FIG. 4). Similarly, but conversely, the positioning of the lower jaw will affect the CC alignment. Consequently, when the patient's lower jaw is held in an optimized position, the patient's CC/CM complex will be maintained in the orthopedically optimized position corresponding to the optimized jaw position.

Figure 5:
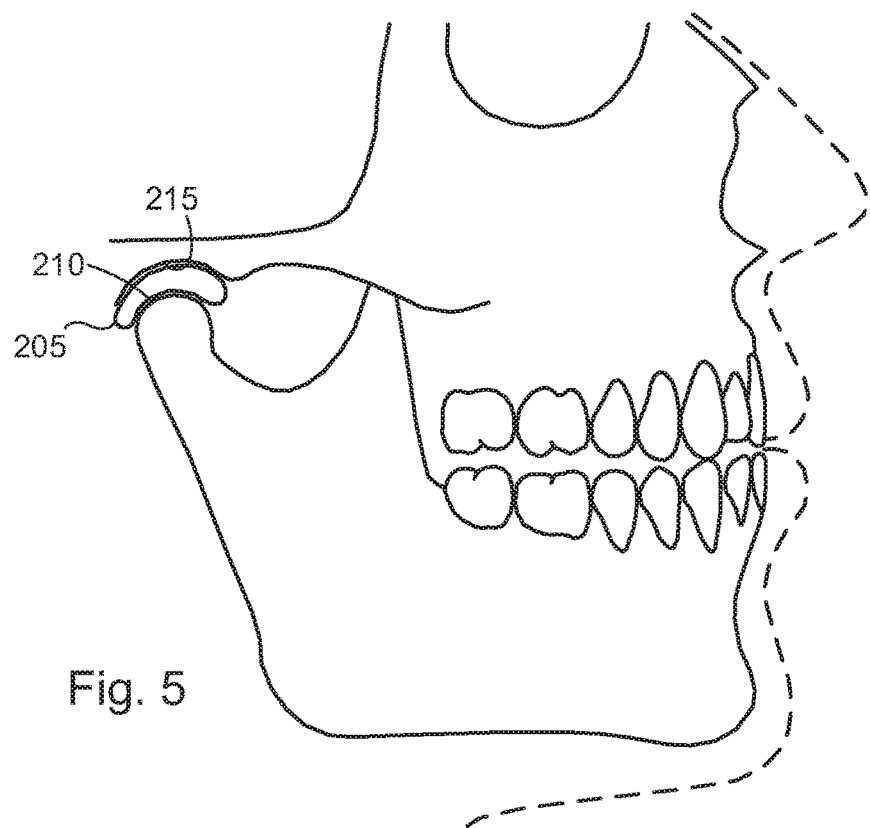
FIG. 5 is a diagram illustrating a patient's jaw at its orthopedically optimized CM relationship in a position that has decompressed the condyle in the glenoid fossa and reducing the disc in the TMJ.

Thus, ideally, a mouthpiece would hold a wearer's jaw in an orthopedically beneficial position as shown in FIG. 5. By maintaining the orthopedically beneficial jaw position, particularly when proprioception of jaw position occurs, orthopedic alignment of the head and upper cervical spine is maintained, neural shear is reduced, range of motion in the major joints is improved, and balance is improved. This reset of orthopedic alignment also minimizes risk of injury.

As shown in FIGS. 4 and 5, an articular disk 205 is positioned between the condyle 210 of the lower jaw and the glenoid fossa 215 of the temporal bone. Normally, as the jaw is opened and closed, the disks move so that they remain between the condyle and the fossa. If, when the jaw is closing and the posterior teeth are coming into terminal contact, the condyle moves up and back, it may compress the TMJ and place load on the posterior portion of the articular disc. This causes ADD. ADD and the corresponding misalignment of the TMJs creates unwanted torque in the upper cervical spine due to nociceptive signaling. This creates reflex contraction of the upper cervical muscles (especially the suboccipital muscle around C1/C2), leading to atlas and axis subluxation and head misalignment, and inducing neural shear.

In order to achieve a beneficial alignment of the jaw in which articular disks 205 are not compressed (and the CC/CM complex consequently moves toward alignment), the present systems and methods employ a formable mouthpiece (which may be referred to herein as an orthopedic alignment device, or OAD) and means for properly aligning the jaw and maintaining this alignment while the mouthpiece is being formed to the user's teeth. The alignment means (e.g., an alignment member that extends laterally across the mouthpiece) is positioned in a gap in the mouthpiece that allows the alignment member to be positioned between the teeth without obstruction from the mouthpiece. After the mouthpiece is formed, the alignment member is removed, and inserts may be positioned in the gap to provide cushioning between the teeth. Additional molding may be performed to mold the inserts to the user's teeth.

In the present systems and methods, rather than applying TENS to deprogram the jaw muscles, an alignment member is positioned in contact with the upper and lower teeth (e.g., distal to upper teeth numbers 6 and 11, and mesial to lower teeth numbers 22 and 27), to urge the jaw toward the orthopedically optimized position. By allowing the alignment member to be positioned in the alignment gap in the moldable portion of the mouthpiece while it is molded to the teeth, a more optimized jaw position will be achieved in molding the OAD than with a conventional mouthpiece in which jaw alignment is uncontrolled. In addition to adjusting the anterior/posterior position of the jaw, the alignment member of the OAD maintains even spacing between the upper and lower teeth on the left and right sides, so that there is no "roll" of the jaw. Preferably, a vertical index of 17-21 mm will be developed in the optimized jaw relationship, or in some situations a minimum of 2 mm of space between the closest approximation of teeth (the closest the upper and lower teeth come to touching each other).

Figure 6:
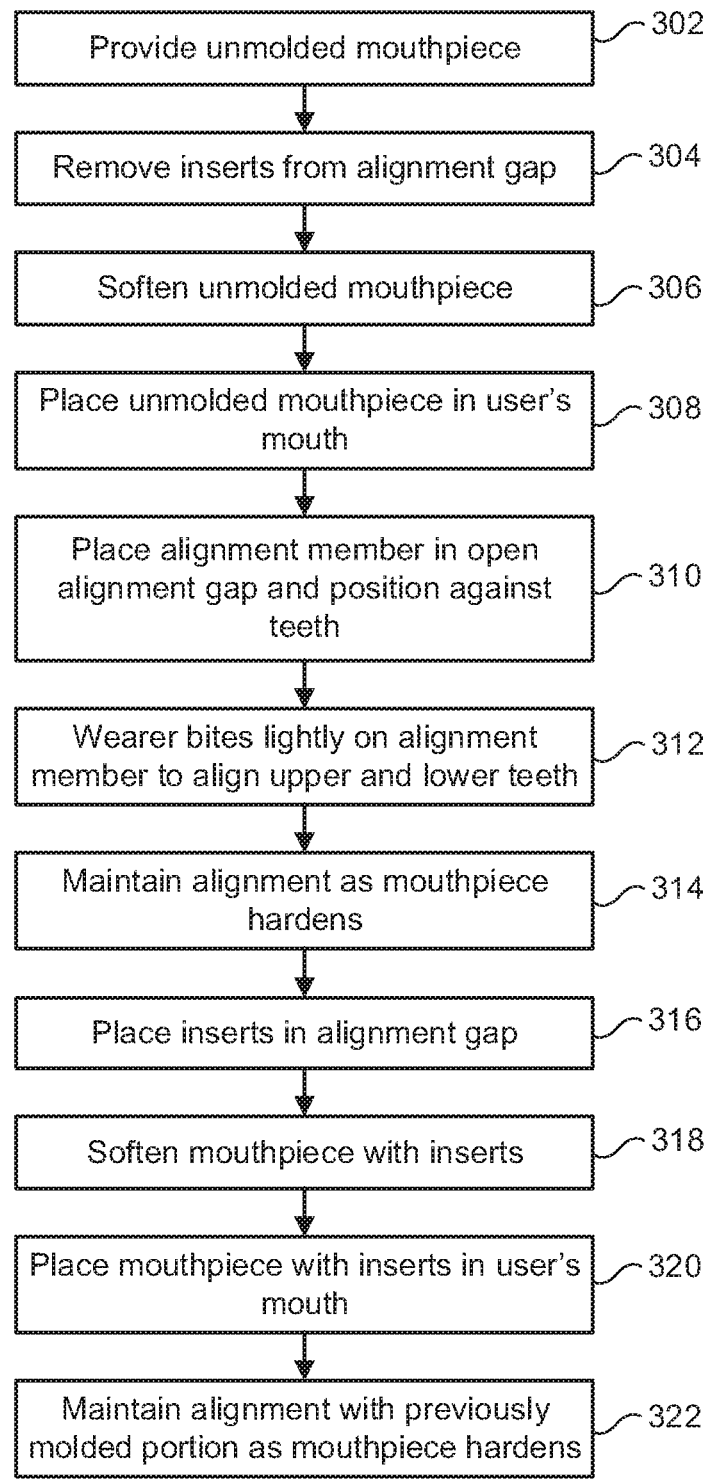
FIG. 6 is a flow diagram illustrating a method for forming an exemplary user-fitted OAD in accordance with one embodiment.
Figure 7A:
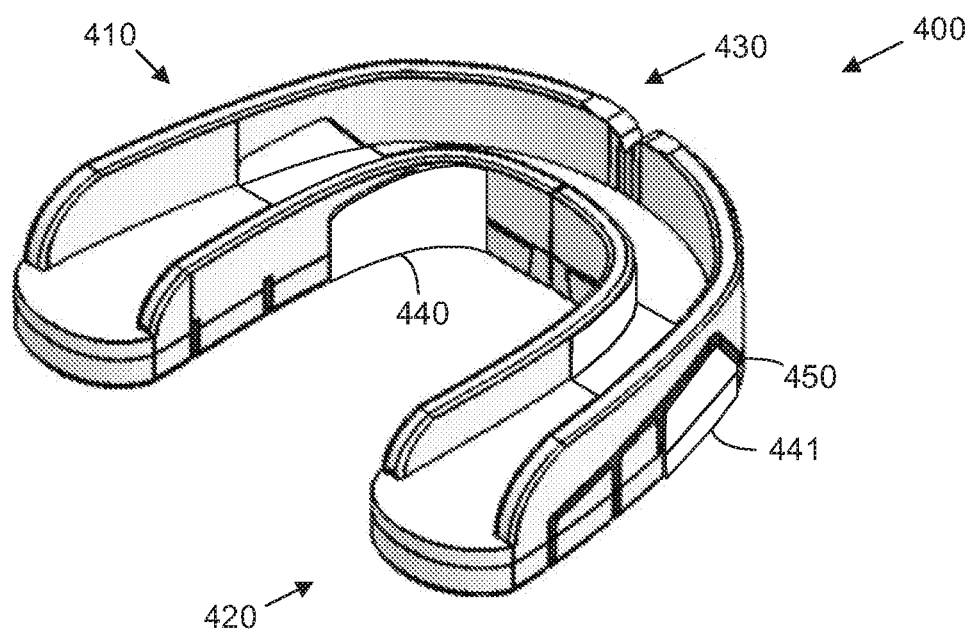
FIGS. 7A-7B are diagrams illustrating an exemplary OAD assembly in accordance with one embodiment.
Figure 7B:
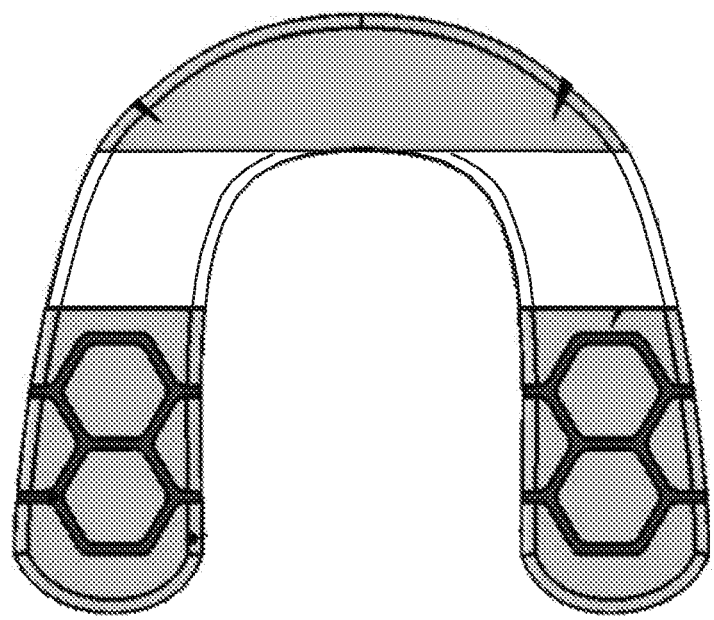

The moldable portion of the OAD can be made from any suitable material as known in the art, such as an EVA (ethylene vinyl acetate) type material, another type of thermoplastic material, or suitable 3D printing materials. The selected material may be formed in accordance with the method illustrated in FIG. 6. In this figure, an unmolded OAD is provided (302). The mouthpiece has a moldable portion that has an alignment gap in it to allow positioning of the alignment member between the teeth when the moldable portion is placed in the wearer's mouth. If inserts are initially positioned in the alignment gap of the moldable portion, they should be removed (304).

The moldable portion is softened by, for example, placing it in a hot water bath for some amount of time (306). The specific steps that are used to soften the material will depend on the manufacturer's recommendations and requirements for the material. The softened moldable portion is then placed in the wearer's mouth (308). The alignment member is positioned laterally within the gap between the user's teeth (310) The alignment member may be positioned between the teeth either before or after the moldable portion is placed in the wearer's mouth. The wearer lightly bites down so that the alignment member contacts the upper and lower teeth (e.g., distal to upper teeth 6 and 11, and lower teeth 22 and 27) and causes the lower jaw to move to a desired aligned position (312). It should be noted that the alignment member is substantially rigid, so that it will not be significantly deformed by the user biting down on it when the mouthpiece is molded. The moldable portion is molded around the wearer's teeth and is then allowed to harden (314).

When the moldable portion has hardened, the moldable portion and the alignment member can be removed the wearer's mouth. Inserts are then positioned in the alignment gap (316). The inserts may be locked into position by retaining features in the inserts and the molded portion of the OAD (e.g., small barbed posts on the inserts that fit into corresponding holes in the moldable portion or a frame in the moldable portion). After the inserts are positioned in the alignment gap, the inserts can be softened (318) to mold them to the canine teeth, although this is not necessary in all embodiments. In one embodiment, the entire assembly is softened (e.g., in a hot water bath). Alternatively, only the front portion of the assembly with the inserts can be softened. The assembly can then be placed back in the wearer's mouth to mold the inserts to the wearer's teeth (320). The previously molded portion of the OAD will serve to maintain the proper orthopedic alignment of the jaw while the inserts are molded to the teeth, so the alignment member is no longer needed for this purpose (322). When the inserts have hardened, the OAD is ready for use.

An exemplary embodiment of the OAD is shown in FIGS. 7-11. Referring to FIGS. 7A-7B, the entire OAD assembly, including an overmold, a frame, and alignment gap inserts is depicted. FIG. 7A is a perspective view of the OAD, while FIG. 7B is a plan view of the underside of the OAD. It can be seen in these figures that OAD 400 is a generally semicircular device that fits around the wearer's teeth. It should be noted that, although the device illustrated in these figures is designed to be formed around the wearer's upper teeth, alternative embodiments may be designed to be formed around the wearer's lower teeth, or around both the upper and lower teeth. In one embodiment, the structure of an OAD designed to be molded to the wearer's lower teeth is substantially the same as the embodiment shown in FIGS. 7-11. In an embodiment designed to be molded to both the wearer's lower teeth and the wearer's upper teeth is substantially the same as the embodiment shown in FIGS. 7-11, except that the vertical walls extend both above the bite portions (to be molded against the wearer's upper teeth) and below the bite portions (to be molded against the wearer's lower teeth).

In this embodiment, OAD 400 includes left (410) and right (420) portions which are molded around the wearer's molars, a front portion 430 that is molded around the wearer's front teeth, and insert portions (440, 441) that may be molded around the wearer's canine teeth. Front portion 430 and left and right portions 410 and 420 are connected to each other and are referred to herein as an overmold. The overmold and the insert portions are made of an EVA-type material or any other suitable material known in the art which can be softened and molded to the wearer's teeth. The overmold in this embodiment is formed over a frame 450 in order to provide some rigidity between the front portion and the right and left portions when inserts 440 and 441 are removed.

Figure 8A:
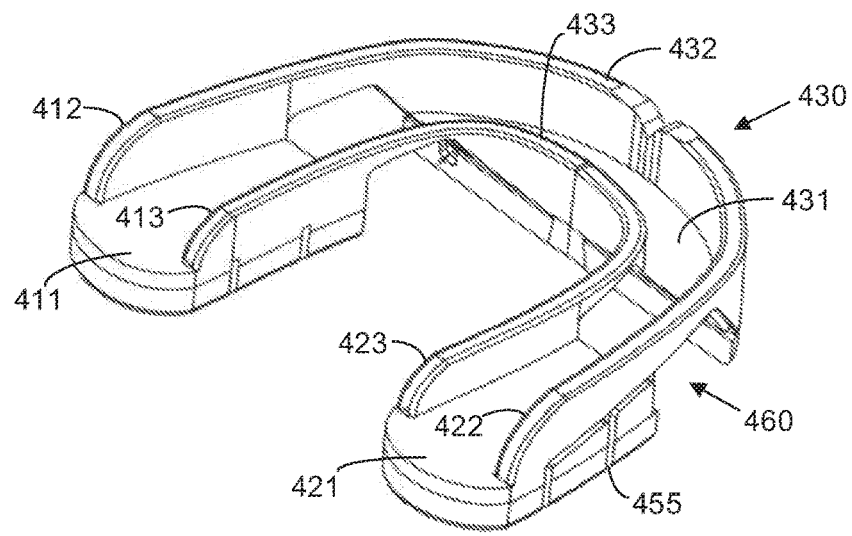
FIGS. 8A-8C are diagrams illustrating an overmold for an exemplary OAD in accordance with one embodiment.
Figure 8B:
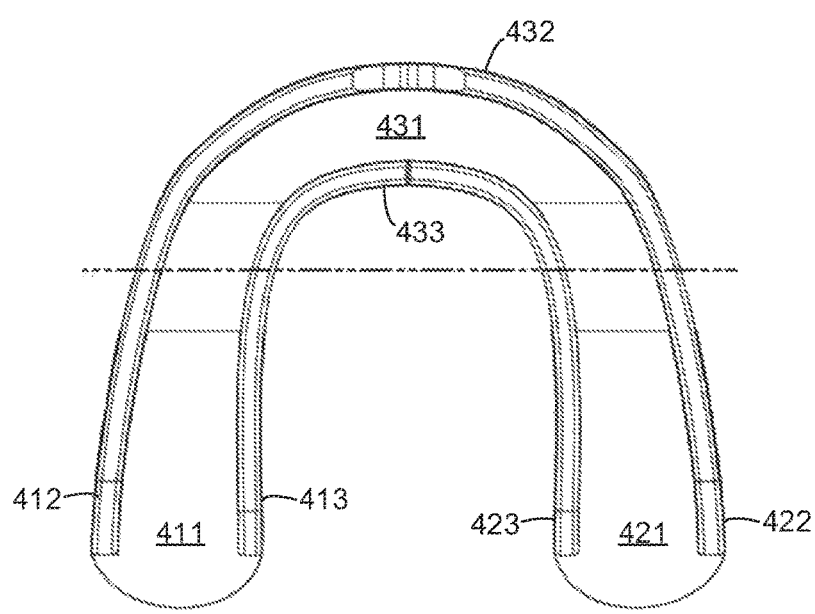
Figure 8C:
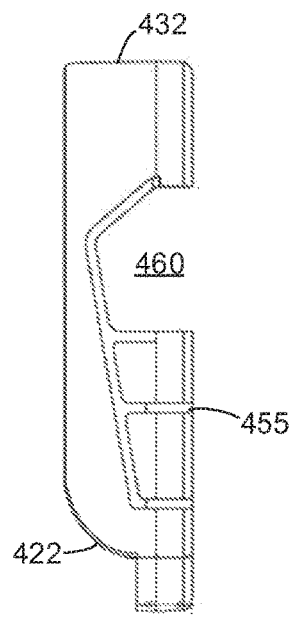

Referring to FIGS. 8A-8C, the overmold is shown without the frame and insert portions. Each of the right and left portions of the overmold has a corresponding bite portion (411, 421) that contacts the bite surfaces of the wearer's molars. Vertical walls extend upward from the sides of the bite portions. Walls 412 and 422 extend upward from the outer edges of bite portions 411 and 421, respectively. Walls 413 and 423 extend upward from the inner edges of bite portions 411 and 421, respectively. Front portion 430 likewise has a bite portion 431 with outer (432) and inner (433) vertical walls extending upward from the corresponding edges of bite portion 431. The bite portions (411, 421, 431) and vertical walls (412, 413, 422, 423, 432, 433) are initially smooth surfaces as depicted in these figures, but subsequent to molding, these surfaces are conformed to the surfaces of the wearer's teeth.

The inner and outer vertical walls of the right and left portions of the overmold are connected to the inner and outer vertical walls of the front portion. In other words, the vertical walls extend across the alignment gap 460 so that the right and left portions and the front portion of the overmold form a single unit. Because the parts of the vertical walls that extend across the alignment gap are relatively thin, they may not have sufficient rigidity to maintain the overall semicircular shape of the overmold when the material of the overmold is softened prior to forming it around the wearer's teeth. Thus, as noted above, a frame is used to provide additional rigidity to the assembly. Small channels or voids (e.g., 455) are formed in the overmold to accommodate the frame. It should be noted that FIG. 11 (an exploded view of the OAD assembly) shows how the frame 450 is inserted into the channels 455 of the overmold in this embodiment.

Figure 9A:
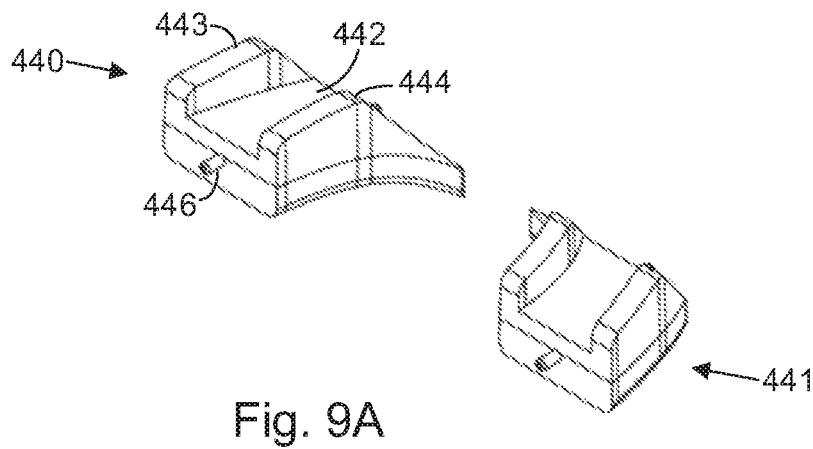
FIGS. 9A-9D are diagrams illustrating alignment gap inserts for an exemplary OAD in accordance with one embodiment.
Figure 9B:
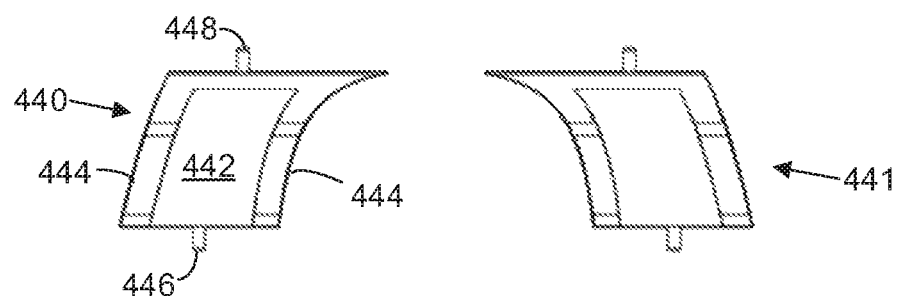
Figure 9C:
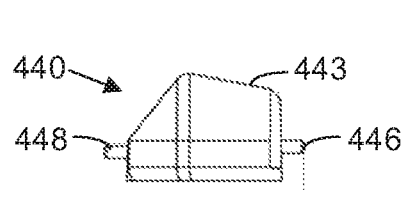

Referring to FIGS. 9A-9C, the alignment gap inserts are shown, apart from the OAD assembly. In this embodiment, two separate inserts (440, 441) are used, although a single insert could be used in alternative embodiments. Left insert 440 is inserted into the alignment gap on the left side of the OAD (between left portion 410 and front portion 430), and right insert 441 is inserted into the alignment gap on the right side of the OAD (between right portion 420 and front portion 430). Each insert includes a bite portion (e.g., 442). When the insert is positioned in the alignment gap and the overmold assembly is placed in the wearer's mouth, the bite portion of the insert is positioned generally between the wearer's upper and lower canine teeth. The insert also has short vertical walls (e.g., 443, 444) that extend upward from the outer and inner edges of the insert's bite portion. The insert is shaped so that when it is positioned in the corresponding alignment gap, generally continuous bite portions and inner and outer vertical walls are formed with the overmold.

Figure 9D:
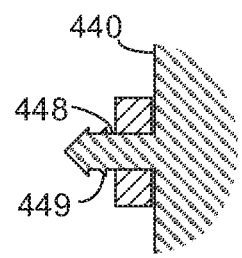

It should be noted that the inserts include positioning features that allow the inserts to be retained within the overmold once they have been inserted. In one embodiment, small posts (446, 448) are provided on the insert. These posts fit within corresponding holes in the overmold and/or frame to hold the insert in position within the alignment gap. In one embodiment, the posts have small barbs (e.g., 449) on their ends, so that when the posts are inserted into the holes, the barbs hold the posts in the holes, as shown in FIG. 9D. This may prevent the inserts from coming out of the alignment gap and presenting a choking hazard. It should be noted that the positioning features may also include various other types of keys and keyways that will maintain the positions of the inserts within the alignment gap.

Figure 10A:
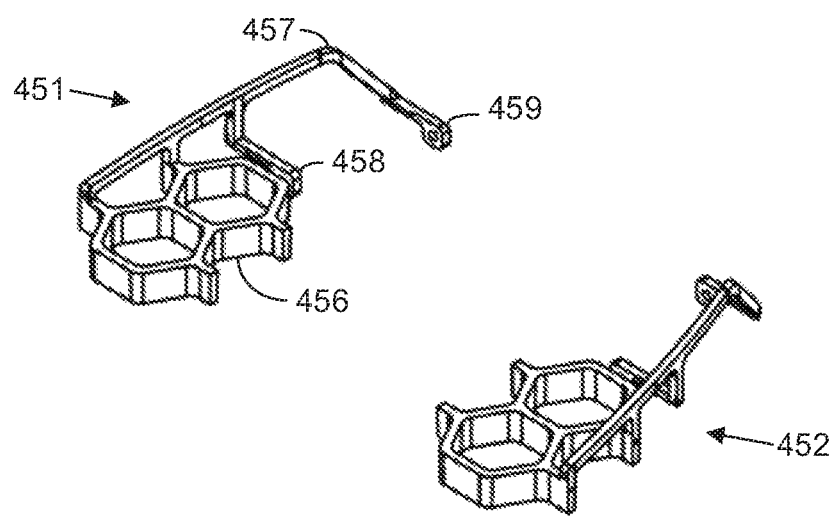
FIGS. 10A-10C are diagrams illustrating a frame for an exemplary OAD in accordance with one embodiment.
Figure 10B:
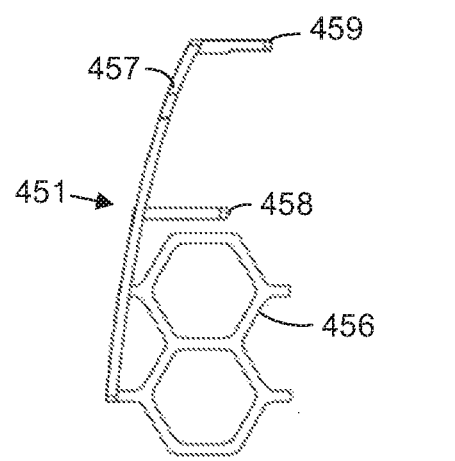
Figure 10C:
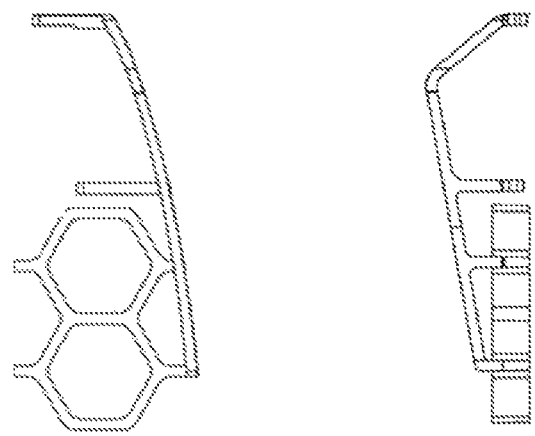
Figure 11:
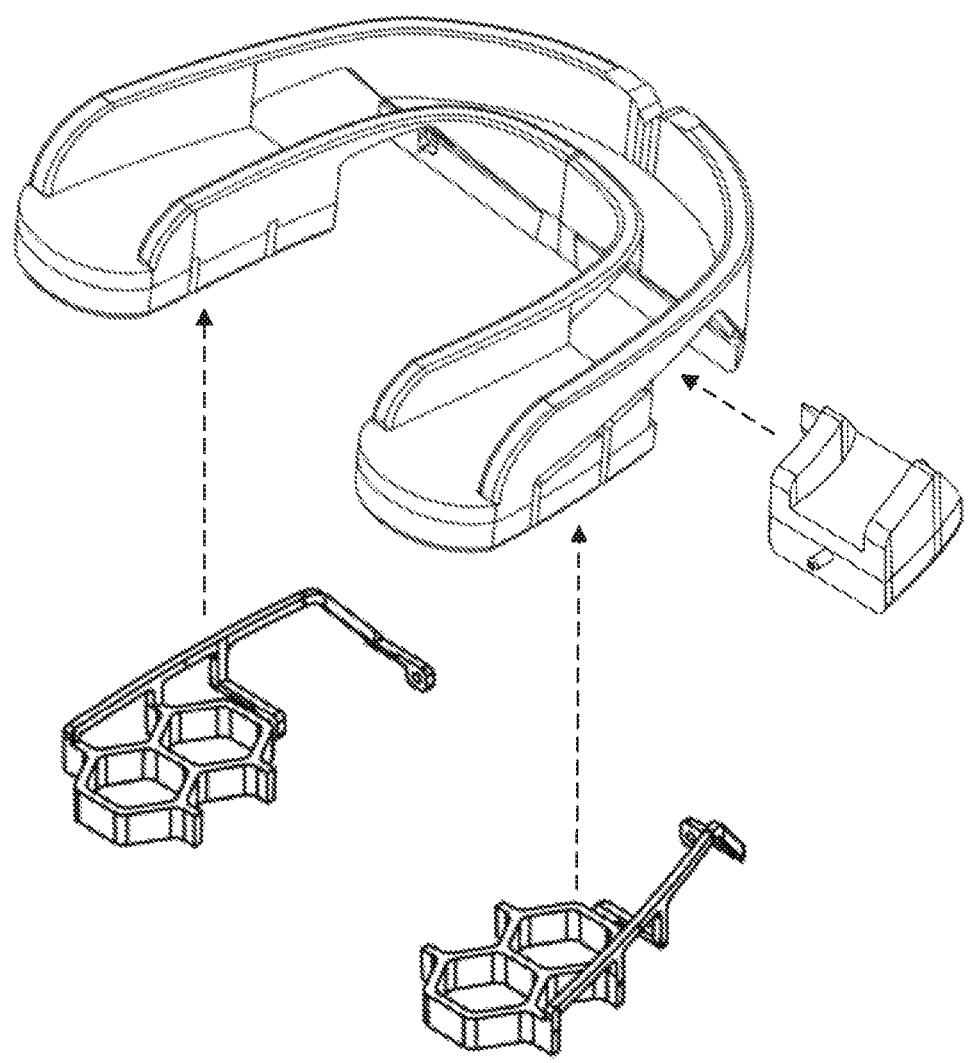
FIG. 11 is a diagram illustrating an exploded view of an overmold assembly for an exemplary OAD in accordance with one embodiment.

Referring to FIGS. 10A-10C, frame 450 is shown apart from the OAD assembly. In this embodiment, the frame includes separate left (451) and right (452) portions. In other embodiments, the frame may be designed as a single unit. Each of the left and right portions of the frame includes a stabilizing portion (e.g., 456) that is inserted into the bite portion of the overmold. The left portion of the frame (451) fits within the left portion of the overmold, and the right portion of the frame (452) fits within the right portion of the overmold. The stabilizing portion may also be referred to as a spacing portion, as it may serve to maintain a minimum or preferred spacing between the wearer's upper and lower molars and/or premolars. The stabilizing portion of the frame is connected to a bridging portion (e.g. 457) of the frame which, when the frame is installed in the overmold, extends across the alignment gap between the left/right rear portion of the overmold (410, 420) and the front portion (430).

Frame 450 is made of a more rigid material than the overmold, so that the bridging portion 457 adds rigidity to the overmold assembly (in comparison to the overmold without the frame). The frame need not be completely rigid or inflexible, but at least the bridging portion should be less flexible so that it will enable the overmold assembly to maintain its generally semicircular shape. It should be noted that the stabilizing portion of the frame may be separately manufactured and inserted into the corresponding bite portion of the overmold, or it may be molded into the bite portion, or formed through any other suitable means. In one embodiment, the stabilizing portion is sized so that it causes a minimum spacing to be maintained between the wearer's upper and lower molars and/or premolars when the device is molded to the wearer's teeth. The minimum spacing is preferably 2-4 mm and in one exemplary embodiment is preferably 3.5 mm. Because the frame is made of a material that is generally less compressible than the overmold (in other words, has a higher durometer than the material of the overmold), it keeps the wearer from biting down too far on the overmold. The frame is not completely incompressible, however, so the bite portion remains compressible and capable of cushioning potential impacts to the jaw.

In this embodiment, frame 450 includes two extensions from bridging portion 457 which are adapted to retain the alignment gap inserts in the overmold assembly. Each of these extensions—rear insert retainer 458 and front insert retainer 459 has a small hole through the end of the extension. The whole is adapted to accept the corresponding retaining post of the alignment gap insert. For example, rear post 446 of insert 440 will extend through the hole in the end of rear insert retainer 458, and the front post 448 of insert 440 will extend through the hole in the end of front insert retainer 459. The overmold may also have holes in it which are aligned with the holes in front and rear insert retainers 459 and 458, so that the posts of the inserts extend through the holes in both the frame and overmold. As noted above, the posts may have barbs so that when they are inserted through the holes, the farms will retain the posts in the holes.

Figure 12:
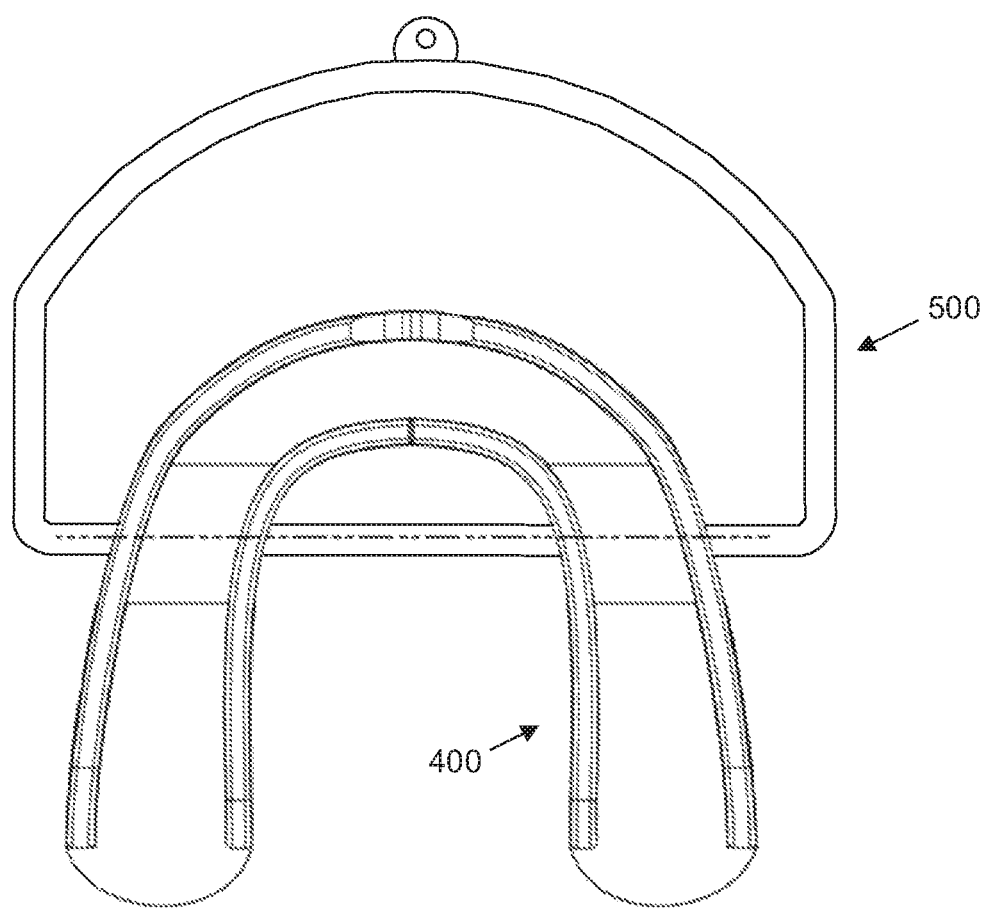
FIG. 12 is a diagram illustrating the positioning of an alignment member with respect to an overmold assembly during molding of the overmold assembly in accordance with an exemplary embodiment.
Figure 13:
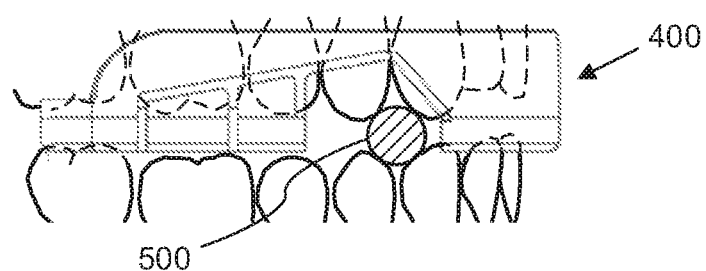
FIG. 13 is a diagram illustrating the positioning of an alignment member with respect to an overmold assembly and the wearer's teeth during molding of the overmold assembly in accordance with an exemplary embodiment.

As described above in connection with FIG. 6, the OAD enables the use of an alignment member to position the wearer's lower teeth with respect to the upper teeth in order to maintain an orthopedically aligned position of the jaw while molding the device. FIGS. 12 and 13 show the positioning of the alignment member 500 with respect to the overmold assembly 400 during the molding process.

It is contemplated that the OAD, when purchased by the wearer, will not have the inserts installed in the alignment gap because the retaining features incorporated into the overmold assembly and the inserts may permanently lock the inserts into position in the alignment gap. If, however, the wearer purchases an embodiment in which the inserts are installed in the alignment gap, the wearer will remove the inserts prior to molding the overmold assembly.

As noted above, the wearer will soften the overmold assembly by means such as placing the assembly in a hot water bath. After the overmold assembly has been softened, the user will place the assembly in his or her mouth, so that the teeth are in contact with the bite portions and are between the inner and outer vertical walls. With the overmold assembly in this position, the alignment gap should be substantially aligned with the gap between the wearer's canine teeth, as shown in FIG. 13. "Substantially aligned" is used here to refer to alignment such that a generally linear alignment member (e.g., a rod) can be positioned laterally across the wearer's mouth between the upper and lower teeth, unobstructed by the overmold assembly. Preferably, the alignment member is not in contact with the overmold assembly. The alignment member need not be centered in the alignment gap of the overmold assembly.

The alignment member is positioned within the alignment gap, and within the gap between the wearer's canine teeth. The alignment member may be positioned in the wearer's mouth either before or after the overmold assembly is positioned in the mouth. Depending upon the wearer's dentition, the alignment member may be situated at various locations within the alignment gap of the overmold assembly. As depicted in FIG. 13, the canine teeth and the alignment member are slightly anterior to the center of the alignment gap of the overmold assembly. When the wearer bites down lightly on the alignment member, the jaw and lower teeth move forward or backward until the alignment member rests in the gap between the teeth, typically distal to teeth 6, 11, 22 and 27). The overmold is then allowed to harden with the jaw in this position. It may be helpful for the wearer to press their tongue against the overmold or to suck the air out of their mouth to help mold the device to the teeth.

The alignment member may have a variety of different shapes and sizes, but as depicted in this figure, the alignment member has a straight rod or dowel with a round cross-section of about 3 mm diameter that extends through the alignment gap. As shown in FIG. 12, the straight portion of the alignment member that extends through the alignment gap is connected at each and to a generally semicircular portion, so that it forms a loop. This loop configuration may serve several purposes. For example, this makes the alignment member large enough that it is not a choking hazard when used to mold the device to a child's teeth. This structure may also keep the alignment member in place in the wearer's mouth during the molding process. For instance, the straight portion of the alignment member may be positioned in the wearer's mouth and the curved portion may be allowed to hang downward against, or under, the wearer's chin so that it prevents is prevented moving out of position.

Referring to FIGS. 14-17, an alternative embodiment of an OAD is illustrated. In this embodiment, the OAD comprises a frame which serves as a tray for moldable material which can be formed to the molars and front teeth of the wearer, the frame having an alignment gap which accommodates an alignment member therethrough during the molding of the material in the tray, and which thereafter accommodates moldable inserts.

Figure 14A:
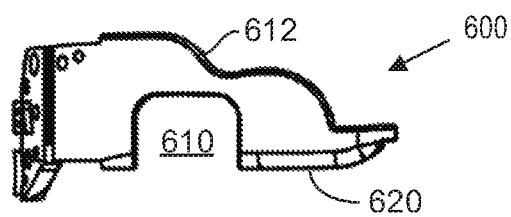
FIGS. 14A-14C are diagrams illustrating the structure of a frame that can be used in some embodiments of an OAD.
Figure 14B:
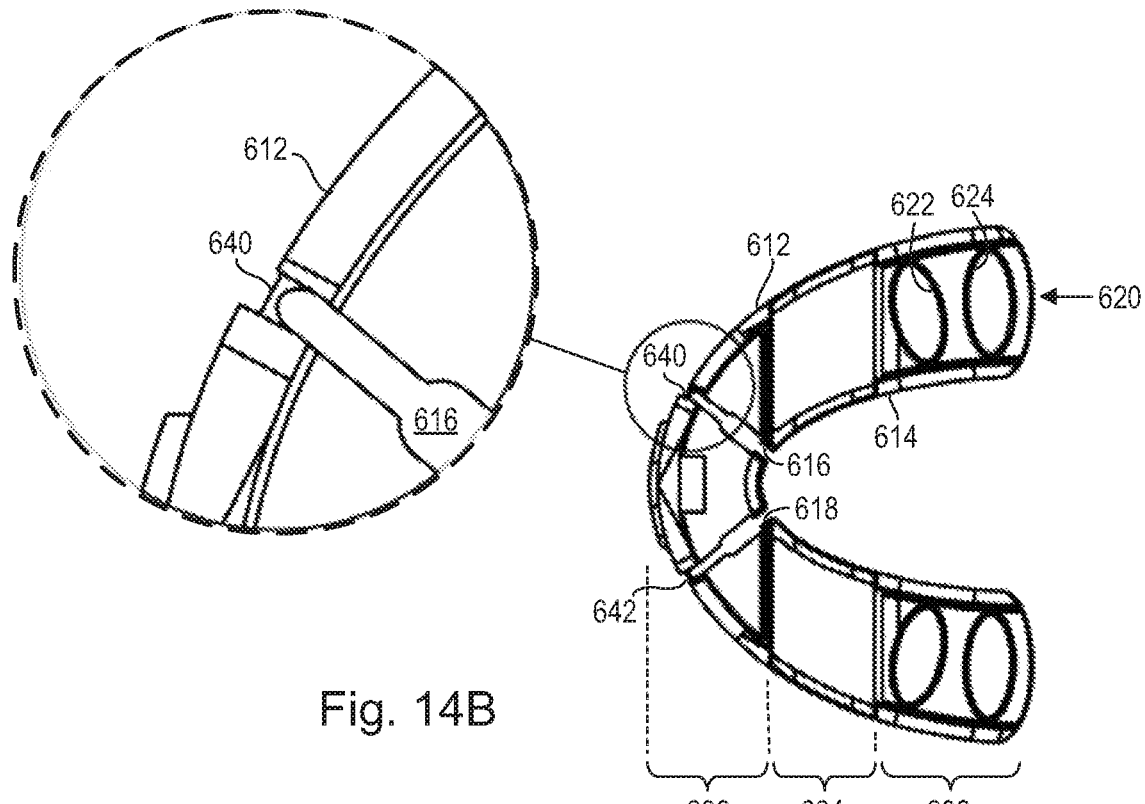
Figure 14C:
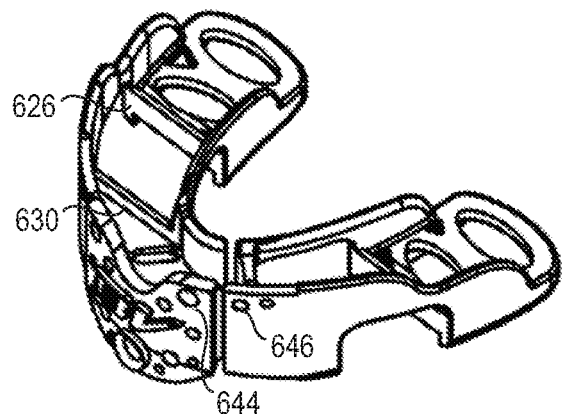

Referring to FIGS. 14A-14C, a frame that can be used in this embodiment of the OAD is shown. FIG. 14A is a side view of the frame, FIG. 14B is a top view of the frame, and FIG. 14C is a front perspective view of the frame. As can be seen in these figures, the frame in this embodiment is not entirely contained within an overmold of moldable material, but instead generally serves as a tray within which the moldable material is positioned. Portions of the frame in this embodiment remain exposed when the moldable material is positioned within the tray and molded to the wearer's teeth.

As shown in FIG. 14B, frame 600 has a rear portion 602 which holds the material that will be molded to the wearer's molars, a central portion 604 that includes the alignment gap 610, and a front portion 606 which holds the material that will be molded to the wearer's front teeth. The frame has an outer wall 612 that extends in a generally semicircular shape around the outer edge of the frame. Although the profile of outer wall 612 varies along its length (see, e.g. FIGS. 14A and 14C), the outer wall is substantially continuous. The frame also has an inner wall 614 which is generally semicircular in shape and extends around the interior of the frame, it can be seen that the inner wall is discontinuous at spaces 616 and 618. This will be described in more detail below in connection with the hinged aspect of the frame. Each of the inner and outer walls extends upward from a floor 620 of the frame which is positioned between the wearer's upper and lower teeth when the OAD is in use.

The rear portion 602 of frame 600 forms a right rear tray and a left rear tray, each of which holds moldable material that will be conformed to the wearer's molars. The floor of each of the right and left rear trays has openings therethrough (e.g. 622, 624 so that the moldable material can extend through the frame and can contact both the upper and lower molars. The moldable material can therefore provide cushioning between the wearer's upper and lower molars. The floor of the frame at the rear trays can nevertheless serve to maintain a minimum spacing between the wearer's molars when the moldable material is molded to the wearer's teeth. The frame may be made of a material that is more rigid than the moldable material, yet is still flexible enough that it does not prevent the moldable material from cushioning impacts to the wearer's jaw. It should be noted that each of the left and right rear trays has a barrier (e.g. 626) which is positioned at the front edge of the respective tray and serves to contain the spread of the moldable material when it is molded to the wearer's teeth. This ensures that the moldable material does not flow forward into the area that will be filled by the inserts that fit into the alignment gaps in the frame (as will be discussed in more detail below).

In the embodiment of FIGS. 14-17, the front portion 606 of frame 600 forms a front tray which holds additional moldable material that will be molded to the wearer's front teeth. Similar to the rear trays, the front tray has barriers (e.g., 630) which serve to contain the spread of the moldable material rearward into the area of the alignment gaps when the moldable material is molded to the front teeth.

The front portion 606 of frame 600 also has two "living hinges" 640, 642. As can be seen in FIG. 14B, each living hinge in this embodiment comprises a narrowed section of outer wall 612 which enables the frame to bend at this point. It should be noted that "living hinge" is used here to refer to a structure that enables portions of the frame to flex at a particular location, rather than flexing along the entire frame (or a substantial portion thereof). The living hinges may comprise thinned spots in the outer wall of the frame, more flexible material at the living hinge location, or the like, and it is not necessary to have a conventional pin-and-knuckle structure as found in a door hinge, piano hinge, etc.

Inner wall 614 and floor 620 are discontinuous, forming spaces 616 and 618 between left, center, and right sections of front portion 606 of the frame. These spaces allow the left, center and right portions of the frame to move with respect to each other as the frame bends at hinges 640 and 642. In other words, without the spaces, the frame would not be able to flex because a continuous floor and/or inner wall would hold the left and right sections of the frame in place and prevent them from moving slightly closer to each other or slightly farther away from each other in comparison to the unflexed position depicted in the figure. This allows the frame to be comfortably molded to wearers who have a wider range of jaw sizes (where the molars are more narrowly, or more widely spaced) without having to provide frames of multiple different sizes. If the frame is flexed at the hinges when the device is molded to the wearer's teeth, the molded material in the front tray will tend to hold the frame in this position.

As can be seen in FIG. 14C, outer wall 612 may include holes therethrough (e.g., 644, 646). The moldable material in the front tray may extend through these holes, thereby helping to maintain the positioning of the moldable material with respect to the frame. The moldable material may extend through these holes prior to molding the material to the wearer's teeth, or the process of molding the material to the wearer's teeth may cause a portion of the material to be forced into/through the holes.

Figure 15:
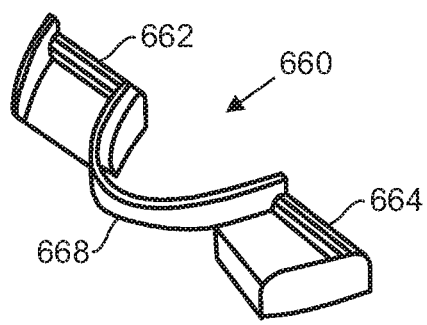
FIG. 15 is a diagram illustrating the structure of an alignment gap insert in accordance with one embodiment.

Referring to FIG. 15, an alignment gap insert 660 is shown. Insert 660 has right and left insert portions (662, 664) which are shaped to fit within the alignment gaps of frame 600. An insert connector 668 extends between insert portions 662 and 664 to hold the two insert portions together so that they can be more conveniently installed in the frame. Connector 668 also serves to retain insert portions 662 and 664 in the alignment gaps in the frame. When insert portions 662 and 664 are lowered into the frame from above, connector 668 rests against inner wall 614 just above the floor of the front tray, preventing the inserts from moving farther downward through the alignment gaps once they are in position.

Figure 16:
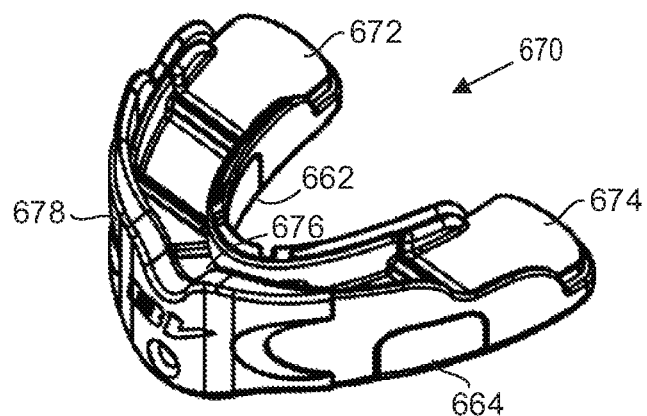
FIG. 16 is a diagram illustrating a perspective view of an assembled OAD in accordance with one embodiment.

Referring to FIG. 16, a perspective view of the assembled OAD is shown. In the assembled OAD 670, a layer of moldable material (672, 674) is positioned in each of the rear trays of the frame and insert portions 662 and 664 are positioned within the alignment gaps of the frame. A layer of moldable material (676, 678) is formed in the front tray and around the outer wall of the front portion of frame. As depicted in this figure, the moldable material has not yet been molded to a wearer's teeth.

Figure 17:
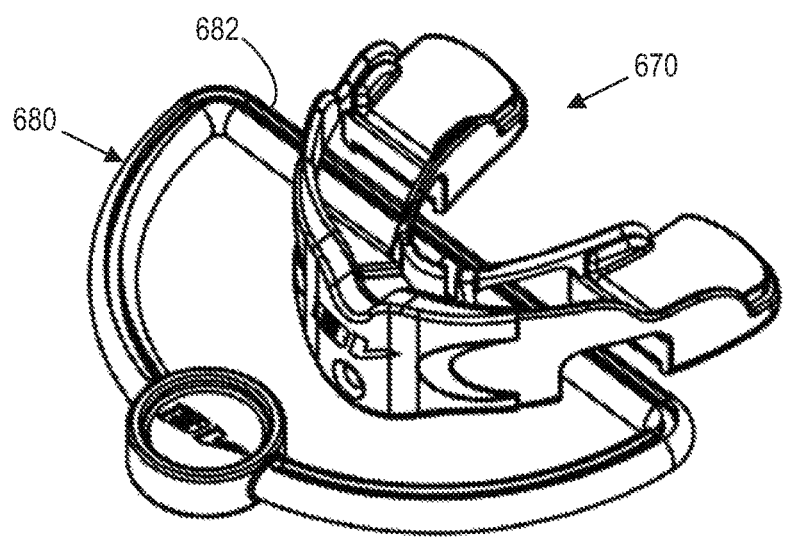
FIG. 17 is a diagram illustrating a perspective view of an alignment ring positioned for use with an OAD in accordance with one embodiment.

Referring to FIG. 17, when the wearer is ready to mold the moldable material of the OAD to the wearer's teeth, the alignment gap inserts are removed, leaving the alignment gaps of the device open. The moldable material is softened, and the OAD is positioned in the wearer's mouth. Alignment ring 680 is positioned with straight alignment member 682 extending through the alignment gaps. The wearer bites down lightly so that straight alignment member 682 contacts the upper and lower teeth (e.g., canines), urging the wearer's jaw toward an optimized, orthopedically aligned position. The moldable material is then conformed to the wearer's teeth and is allowed to harden (stiffen) in this molded shape. When the moldable material has stiffened in the molded shape, the alignment member is removed, and the alignment gap inserts may be positioned in the alignment gaps. The wearer may wish to mold the alignment gap inserts by softening the material of the inserts, positioning the inserts in the alignment gaps, and placing the OAD in the wearer's mouth, with the wearer biting down slightly on the OAD. Since the moldable material on the frame of the OAD has already been molded into an orthopedically aligned position, this material will maintain the wearer's jaw in this position while the inserts are molded to the teeth contacting the inserts. It should be noted that the OAD may be used without the inserts, with unmolded inserts, or with molded inserts.

Figure 18A:
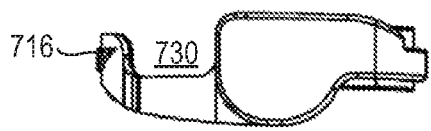
FIGS. 18A-18C are diagrams illustrating alternative embodiment of an OAD adapted to be molded to a wearer's lower molars in accordance with one embodiment.
Figure 18B:
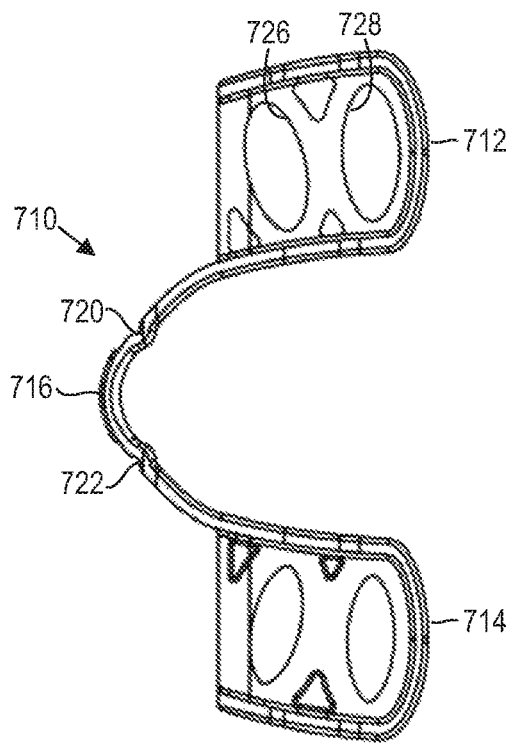
Figure 18C:
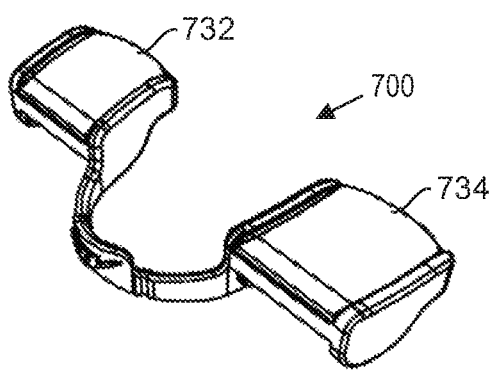
Figure 19:
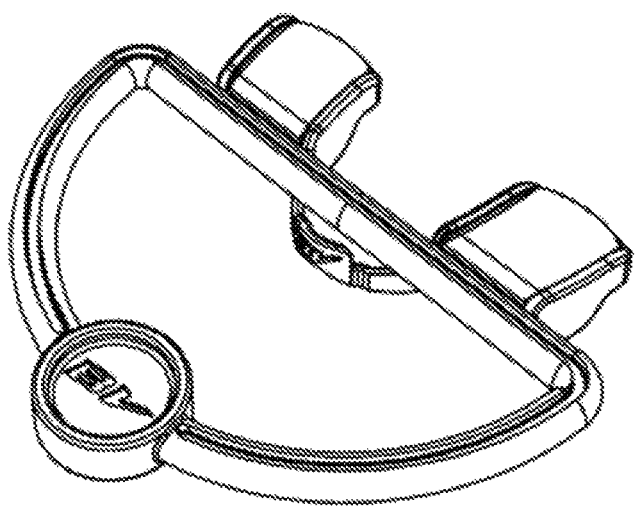
FIG. 19 is a diagram illustrating a perspective view of an alignment ring positioned for use with the OAD of FIGS. 18A-18C.

Referring to FIGS. 18-19, another alternative embodiment of an OAD in accordance with some embodiments is shown. FIG. 18A is a side view of the OAD, FIG. 18B is a top view of the frame used in this OAD, and FIG. 18C is a front perspective view of the OAD with moldable cushioning material positioned on the frame. FIG. 19 is a perspective view of the OAD with an alignment ring positioned for molding the OAD.

As depicted in these figures, OAD 700 is rear-only design which provides cushioning only between the upper and lower molars of the wearer—no cushioning is provided between the wearer's front teeth. Accordingly, frame 710 includes right and left rear trays (712, 714) which are substantially similar to those of the frame depicted in FIG. 14B, but no front portion. Moldable material (732, 734) is positioned in the trays to form bite pads which provide cushioning between the wearer's upper and lower molars. The moldable material extends through holes (e.g. 726, 728) in the frame so that the moldable material is retained on the frame and contacts both the upper and lower molars to provide cushioning during an impact to the jaw. In this embodiment, OAD 700 is designed to be retained on the wearer's lower molars, so a larger portion of the moldable material may be positioned on the underside of frame 710 so that it can be molded around the wearer's lower molars.

Frame 710 includes a frame connector 716 which is connected to each of rear trays 712 and 714 to hold them substantially in place with respect to each other. When OAD 700 is positioned in the wearer's mouth, frame connector 716 is positioned behind the wearer's lower front and canine teeth. As can be seen in FIG. 18A, connector 716 rises slightly behind the front teeth, but an alignment gap 730 is maintained anterior to the bite pads so that an alignment member can be positioned between the wearer's canine teeth to move the jaw to an orthopedically aligned position when the moldable material is molded to the wearer's molars. In this embodiment connector 716 includes a set of hinges (720, 722) which allow the connector to flex somewhat so that the spacing between the right and left bite pads (on rear trays 712, 714) can be increased or decreased to adapt to the lateral spacing of the wearer's right and left molars. The hinges in this example comprise indentations in connector 716 reduce the thickness of the connector at these points and which allow the connector to bend at these points while the remainder of the connector is more rigid and retains its shape.

Referring to FIG. 19, OAD 700 is shown with an alignment ring positioned in the alignment gap to illustrate the use of the alignment ring during molding of the OAD to the wearer's teeth. When the wearer wishes to mold the OAD, the moldable material is softened (e.g., by heating the material), the OAD is positioned in the wearer's mouth, and alignment ring 780 is positioned with straight alignment member 782 in alignment gap 730, extending between the wearer's canine teeth. The wearer bites down lately on OAD 700 and alignment member 782. Contact between the wearer's canine teeth and alignment member 782 urges the jaw toward a more optimized, orthopedically aligned position, and the moldable material conforms to the molars with the jaw in this position. The moldable material Is allowed to harden/stiffen with the jaw in this position. Alignment ring 780 is then removed, and OAD 700 is ready for use.

It should be noted that there may be many variations of the foregoing embodiments that are within the scope of the claims below. For example, although the embodiments described above use a single, dowel-shaped alignment member, alternative embodiments may use an alignment member having a different shape. For example, the cross-section of the alignment member may be square, or have some other shape instead of being round. Further, the alignment member may vary in diameter (or size, if the alignment member is not round). Additionally, multiple alignment members could be used instead of a single one. Many other variations are also possible within the scope of the invention.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A method for forming user-customizable orthopedic alignment device (OAD), the method comprising:
providing a moldable mouthpiece having at least a right section and a left section, wherein each of the right and left sections has a bite portion that includes a moldable material, the moldable mouthpiece having an alignment gap;
placing the moldable mouthpiece in a user's mouth with the bite portions of the right and left sections positioned between the user's upper and lower molars and with the alignment gap positioned substantially in alignment with the user's canine teeth;
placing an alignment member between the user's canine teeth, wherein the alignment member is positioned in the user's mouth within the alignment gap of the moldable mouthpiece and within a gap between the user's canine teeth;
lightly biting down on the alignment member so that the alignment member contacts the user's upper and lower canine teeth, wherein contact pressure between the user's teeth and the alignment member urges the jaw toward an orthopedically aligned position, and wherein the bite portion of the right and left sections of the moldable mouthpiece are molded to a plurality of the user's molars; and
allowing the moldable mouthpiece to harden.

2. The method of claim 1, wherein the moldable mouthpiece further comprises a frame, wherein the frame includes right and left rear trays that are adapted to retain the moldable material thereon, wherein each of the right and left rear trays has a thickness of at least 2 mm, wherein the method further comprises molding the first moldable material to the user's teeth while the right and left rear trays prevent the user's upper molars from being positioned closer than 2 mm from the user's lower molars.

3. The method of claim 2, wherein the moldable mouthpiece further comprises a rear-only mouthpiece in which the frame has a frame connector connected between the right and left sections of the frame, wherein the method further comprises positioning the frame connector posterior to the user's lower front teeth when the moldable mouthpiece is positioned in the user's mouth.

4. The method of claim 3, wherein the frame connector includes one or more living hinges that enable portions of the frame to pivot with respect to each other, wherein the method further comprises adjusting a spacing between the right section and the left section of the frame by flexing the frame connector at the one or more living hinges.

5. The method of claim 1, further comprising softening the moldable mouthpiece prior to placing the moldable mouthpiece in the user's mouth.

6. The method of claim 1, wherein placing the alignment member between the user's canine teeth comprises positioning the alignment member laterally in the user's mouth.

\* \* \* \* \*